(12) United States Patent
Peruzzo

(10) Patent No.: US 11,596,730 B2
(45) Date of Patent: *Mar. 7, 2023

(54) PACKAGING FOR MEDICAL CONTAINERS

(71) Applicant: Becton Dickinson France, Le Pont de Claix (FR)

(72) Inventor: Gregory Peruzzo, Prunieres (FR)

(73) Assignee: Becton Dickinson France, Le Pont de Claix (FR)

( * ) Notice: Subject to any disclaimer, the term of this patent is extended or adjusted under 35 U.S.C. 154(b) by 55 days.

This patent is subject to a terminal disclaimer.

(21) Appl. No.: 17/142,000

(22) Filed: Jan. 5, 2021

(65) Prior Publication Data

US 2021/0121621 A1 Apr. 29, 2021

Related U.S. Application Data

(63) Continuation of application No. 14/112,568, filed as application No. PCT/EP2012/057195 on Apr. 19, 2012, now Pat. No. 11,000,643.

(30) Foreign Application Priority Data

Apr. 20, 2011 (EP) .................................... 11305474

(51) Int. Cl.
*A61M 5/00* (2006.01)
*B65D 51/18* (2006.01)
*B65D 77/20* (2006.01)
*B65B 5/06* (2006.01)

(52) U.S. Cl.
CPC .............. *A61M 5/002* (2013.01); *B65B 5/068* (2013.01); *B65D 51/185* (2013.01); *B65D 77/2024* (2013.01); *B65D 2251/0031* (2013.01); *B65D 2251/0062* (2013.01); *B65D 2251/0093* (2013.01)

(58) Field of Classification Search
CPC ...... A61M 5/002; B65B 5/068; B65D 51/185; B65D 77/2024; B65D 2251/0031; B65D 2251/0062; B65D 2251/0093; B65D 77/20; B65D 51/18; A61J 1/00
USPC .......................................................... 206/364
See application file for complete search history.

(56) References Cited

U.S. PATENT DOCUMENTS

| | | |
|---|---|---|
| 2,759,656 A | 8/1956 | Abrams |
| 2,993,590 A | 7/1961 | Denton |
| 3,061,091 A | 10/1962 | Wichman |
| 3,154,215 A | 10/1964 | Vesconte |

(Continued)

FOREIGN PATENT DOCUMENTS

| | | |
|---|---|---|
| DE | 1234088 A1 | 4/1994 |
| WO | 9319986 A1 | 10/1993 |

(Continued)

*Primary Examiner* — J. Gregory Pickett
*Assistant Examiner* — Jenine Pagan
(74) *Attorney, Agent, or Firm* — The Webb Law Firm

(57) ABSTRACT

Packaging for medical containers, including a tub having a peripheral wall, a sealing cover sealable on an opening of the tub and a sealing envelope able to protect the sealing cover. The sealing envelope includes: a lower sealing part, having a frame able to be sealed to the peripheral wall of the tub, and a bonding surface that extends outwards from the frame, and an upper sealing part sealed on the bonding surface to enclose the opening of the tub and the sealing cover.

8 Claims, 5 Drawing Sheets

(56) References Cited

U.S. PATENT DOCUMENTS

| | | | |
|---|---|---|---|
| 3,202,277 A | 8/1965 | Lewi | |
| 3,229,813 A | 1/1966 | Crowe, Jr. et al. | |
| 3,301,392 A | 1/1967 | Regan, Jr. | |
| 3,339,724 A | 9/1967 | Hickin | |
| 3,390,766 A | 7/1968 | Stockdale | |
| 3,486,615 A | 12/1969 | Woskin | |
| 4,463,893 A | 8/1984 | Brunone et al. | |
| 4,482,053 A | 11/1984 | Alpern et al. | |
| 4,863,016 A * | 9/1989 | Fong | A61M 25/002 206/439 |
| 6,364,113 B1 | 4/2002 | Faase, Jr. et al. | |
| 6,622,864 B1 | 9/2003 | Debbs et al. | |
| 6,830,149 B2 | 12/2004 | Merboth et al. | |
| 7,100,768 B2 | 9/2006 | Grimard et al. | |
| 7,303,073 B2 | 12/2007 | Raynal-Olive et al. | |
| 8,251,214 B2 * | 8/2012 | Wade | B65D 73/0092 206/459.5 |
| 2003/0217949 A1 | 11/2003 | Schamante | |
| 2005/0103666 A1 | 5/2005 | Grimard et al. | |
| 2005/0115204 A1 | 6/2005 | Kiel et al. | |
| 2005/0226763 A1 | 10/2005 | Raynal-Olive et al. | |
| 2006/0201843 A1 | 9/2006 | Kellar et al. | |
| 2007/0209957 A1 | 9/2007 | Glenn et al. | |
| 2008/0172988 A1 | 7/2008 | Hwang | |
| 2008/0173563 A1 | 7/2008 | Perot | |
| 2009/0100802 A1 | 4/2009 | Bush et al. | |
| 2011/0240503 A1 * | 10/2011 | Bailey | B65D 73/0007 206/469 |
| 2012/0318695 A1 * | 12/2012 | Seber | B32B 5/028 206/524.6 |

FOREIGN PATENT DOCUMENTS

| | | |
|---|---|---|
| WO | 0240065 A1 | 5/2002 |
| WO | 03089028 A1 | 10/2003 |

* cited by examiner

PACKAGING FOR MEDICAL CONTAINERS

CROSS-REFERENCE TO RELATED APPLICATION

The present application is a continuation of U.S. patent application Ser. No. 14/112,568, filed Oct. 18, 2013, entitled "Packaging for Medical Containers", which is a national stage application under 35 U.S.C. § 371 of International Patent Application Serial No. PCT/EP2012/057195, filed Apr. 19, 2012 entitled "Packaging for Medical Containers", and claims priority to European Patent Application No. 11305474.6 filed on Apr. 20, 2011, the entire disclosures of each of which are hereby incorporated by reference.

BACKGROUND OF THE INVENTION

Field of the Invention

This invention is directed to a packaging for medical containers such as, for example, syringes or cartridges. Each container notably comprises a cylindrical body, in particular tubular, and an "upper surface" located at or near the proximal end of this cylindrical body. This upper surface is generally formed by a flange that can be integrally formed with the cylindrical body or that can be a separate piece mounted on this body.

In the present text, the distal end of a component or of a device means the end furthest away from the hand of the user and the proximal end means the end closest to the hand of the user, when the component or device is in the use position, i.e. when the user is injecting a medicine contained in the container into his body or into another patient's body. Similarly, in the present text, the terms "in the distal direction" and "distally" mean in the direction of the injection of the medicine, and the terms "in the proximal direction" and "proximally" mean in the direction opposite to the direction of injection.

Description of Related Art

Often, the containers must be transported from one site to another, when they are manufactured in one site and filled in another site, or, less frequently, when they are manufactured and filled in the same site and must be delivered, once filled, to another site.

For this transportation, the containers are usually put in a "global packaging" comprising a grouping tray or nest, hereinafter "nest", a packaging tub, hereinafter "tub", a sealing cover and a plastic bag, hereinafter "header bag" to insure the sterility. The combination of the nest, the tub and the sealing cover will be cited hereinafter as "packaging" while the tub will correspond to an empty tub.

The nest can have various shapes according to the type of containers received: it can comprise openings that can be or not coaxially surrounded by chimneys for receiving the cylindrical bodies of the containers with flanges, these flanges leaning on the upper ends of the chimneys. Alternatively, the nest can have specific openings for receiving cartridges that would be in contact with the bottom of the tub. In another embodiment, the nest can have chimneys with closed bottoms for receiving containers without flanges; the nest can also be made in a resilient material and have openings in which the containers are frictionally maintained. In the following description, the nest described is the one with openings coaxially surrounded by chimneys for receiving containers with flanges.

The tub includes a peripheral outer flange levelled with its upper opening, for the sealing of the sealing cover. In use, the nest is placed into the tub which is sealed with a sealing cover and sterilised. Then, series of global packagings are stacked into a box, bottom up, for example, a cardboard or a plastic box with an intermediate sheet placed between two series of global packagings, a series being defined as a row of several global packagings.

The header bag can be a classical header bag (e.g. made of plastic including a porous part). Alternatively, the header bag can have a reinforced part positioned in such manner that the header bag gets a function of load spreader. This reinforced part can be interdependent or not with the bag, it can be in moulded or thermoformed plastic, and it can be placed inside or outside the header bag. This reinforced part can be for example at least one thermoformed plastic plate placed inside the bag below and/or above the tub. This reinforced load spreader header bag protects the containers packaged into the packaging.

When received at destination, the global packagings are extracted from the box and flipped bottom down, the header bag is open, the tub is extracted from the header bag and unsealed. Then, the nests are extracted therefrom and the containers can be filled and/or handled.

This existing packaging is satisfactory in general but presents some drawbacks.

Indeed, the header bag has a significant risk of perforation during transportation, which creates a risk of contamination of the packaging.

Moreover, this bag is relatively bulky and therefore limits the number of packaging that can be stacked in a single box.

In addition, due to its size, this header bag wrinkles and folds during transportation, which implies, when opening the packaging, an additional step of manually tensioning the edge thereof, intended to be cut by an automatic machine.

The main purpose of this invention is to overcome these drawbacks.

SUMMARY OF THE INVENTION

The packaging concerned comprises, in a way known per se, a tub having a peripheral wall, a sealing cover sealable on an opening of the tub and a sealing envelope adapted to protect the sealing cover against perforation.

According to the invention, said sealing envelope comprises:
a lower sealing part, having
a frame adapted to be sealed to the peripheral wall of the tub, and
a bonding surface that extends outwards from the frame, and
an upper sealing part sealed on said bonding surface to cover the opening of the tub and said sealing cover.

In the present text, the terms "lower" and "upper" designate something that is respectively "closer" and "farther" from the bottom of the tub.

Thus, the packaging, according to the invention, does not include a header bag enclosing the whole tub but (i) a lower sealing part having a frame adapted to be sealed to the peripheral wall of the tub, that comprises a bonding surface, and (ii) an upper sealing part intended to be sealed on said bonding surface of the lower sealing part. These two sealing parts, when sealed, enclose the opening of the tub and the sealing cover.

The sealing envelope, thus formed, has no risk of perforation during transportation, since the two lower and upper sealing parts are tightly bonded one to the other. This sealing envelope is moreover compact and saves space in the box. In addition, the edges of said upper and lower sealing parts are relatively rigid because these parts are bonded one on the other which does not implies, at the time of opening the packaging, an additional step of manually tensioning an opening edge.

The term "sealing" as used in the present description means any way of tightly joining two parts, e.g. bonding, stamping, gluing, heat-sealing or welding.

According to one possibility, said lower sealing part and upper sealing part are independent from one another. Said upper sealing part is fixed to said lower sealing part once the latter is positioned on the tub.

Alternatively, said upper sealing part is connected to said lower sealing part and is movable with respect to the latter between a first position, in which it does not prevent from sealing the lower sealing part on the lower part of the tub, and a second position in which it is moved over said lower sealing part and is able to be sealed to said lower sealing part.

Said frame of said lower sealing part could exhibit a non-planar shape, including a first peripheral portion adapted to surround the peripheral wall of the tub and to be sealed thereto, and a second peripheral portion in the shape of an outer flange, this outer flange being extended outwards to form said bonding surface.

Preferably, however, the peripheral wall of the tub includes an outer sealing flange around said opening, the lower sealing part having an opening allowing the insertion of the tub, and having an inner peripheral portion forming said frame, dedicated to be sealed to the inferior surface of said outer sealing flange, and an outer peripheral portion forming said bonding surface, extending around the outer edge of the outer sealing flange when said lower sealing part is sealed to said inferior surface.

Said lower and upper sealing parts are preferably flat sheets. In this case, said lower sealing part and said upper sealing part are preferably formed from a single piece of flat material and are connected one another through a folding edge.

Preferably, said lower sealing part and/or said upper sealing part are made of a heat-sealable material, so that their mutual bonding can be achieved by heat sealing.

Preferably, said lower sealing part and/or said upper sealing part are made of a heat sealable material, or are coated with a heat-sealable material, so that said lower sealing part is able to be heat-sealable to said outer sealing flange.

Otherwise, said lower sealing part and said upper sealing part can be mutually bonded with an adhesive.

Said upper sealing part can contain at least a window of permeable and porous material, permeable to a sterilization medium but not to the ambient contamination.

Said permeable and porous material of the upper sealing part can be Tyvek®.

The invention will be better understood and other characteristics and advantages thereof will become evident, with reference to the attached schematic drawings, representing, by way of non-limiting and not exhaustive examples, embodiments of the packaging.

DESCRIPTION OF THE INVENTION

Figure 1:
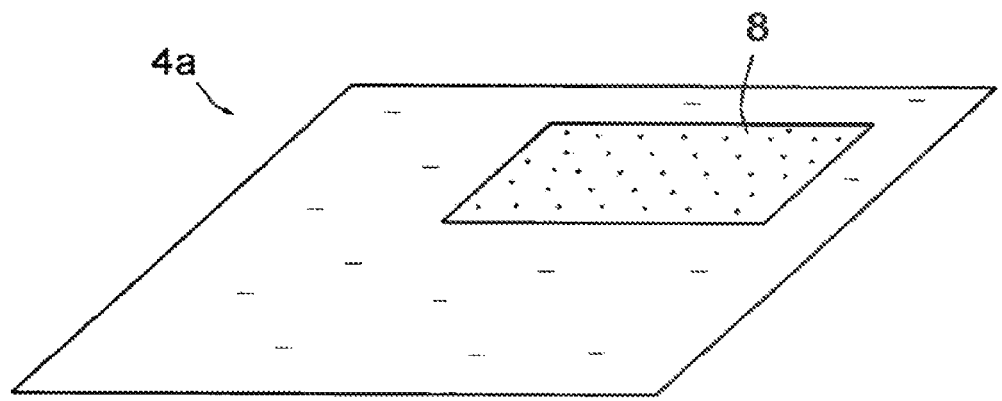
FIG. 1 is a perspective view of an upper sealing part of a sealing envelope included in the packaging according to a first embodiment.

FIGS. 3A-5 show a packaging 1 for medical containers such as, for example, syringes or cartridges, comprising a grouping tray or nest (not shown), hereinafter "nest", a packaging tub 2, hereinafter "tub", a sealing cover 3 and a sealing envelope 4 formed by an upper sealing part 4a and a lower sealing part 4b.

The nest comprises openings coaxially surrounded by chimneys for receiving the cylindrical bodies of the containers, until the flanges thereof abut the upper ends of the chimneys. Such a nest is well known and does not form part of the invention, so it is not particularly described here. Reference can be made to the documents N° WO 03/089028 or WO 02/40065, for example, in the name of the applicant, which show such nests.

Figure 3A:
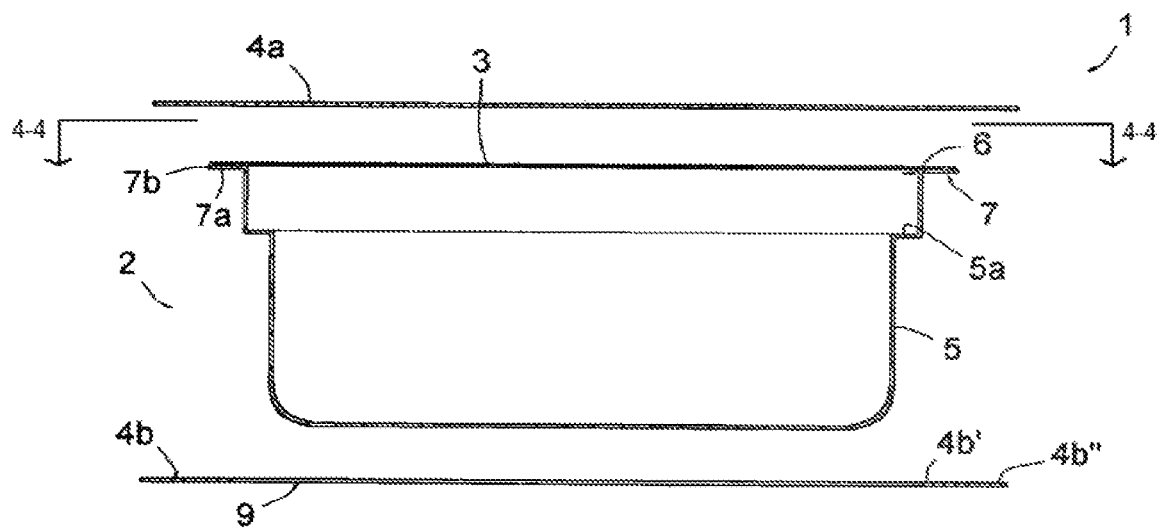
FIG. 3A is a side view of a tub with the upper and lower sealing parts before bonding these upper and lower parts to this tub.

As described on FIG. 3A, the tub 2 is a container having a body 5 able to contain the nest and the medical containers, which has an inner shoulder 5a for receiving the nest. The tub 2 has an upper peripheral wall 2a delineating an upper opening 6 and including a peripheral outer flange 7 levelled with this upper opening 6, for the sealing of the sealing cover 3. The tub 2 is integrally formed by a single part of moulded plastic material.

The sealing cover 3 is formed by a sheet of suitable heat sealable material, in particular by a sheet of high-density polyethylene fibers sold under the trademark_Tyvek®, and is sealed on the upper peripheral wall 2a or on the outer flange 7 of the tub 2 by heat welding.

In reference to FIGS. 1 and 3A, the upper sealing part 4a of the sealing envelope 4 is formed by a sheet of a material suited to protect the cover 3 against perforation and includes a window 8 made of a material permeable to a sterilization medium but not to the ambient contamination (this feature is well known in itself). This upper sealing part 4a has dimensions such that it is able to extend beyond the periphery of the outer edge of the flange 7 and to form, beyond the latter, a peripheral bonding surface designed to be bonded to the lower sealing part 4b by heat welding.

The upper sealing part 4a of the sealing envelope can be made of a flat or a thermoformed sheet of a more or less rigid material (e.g. PET, HPDE, etc.).

Figure 2:
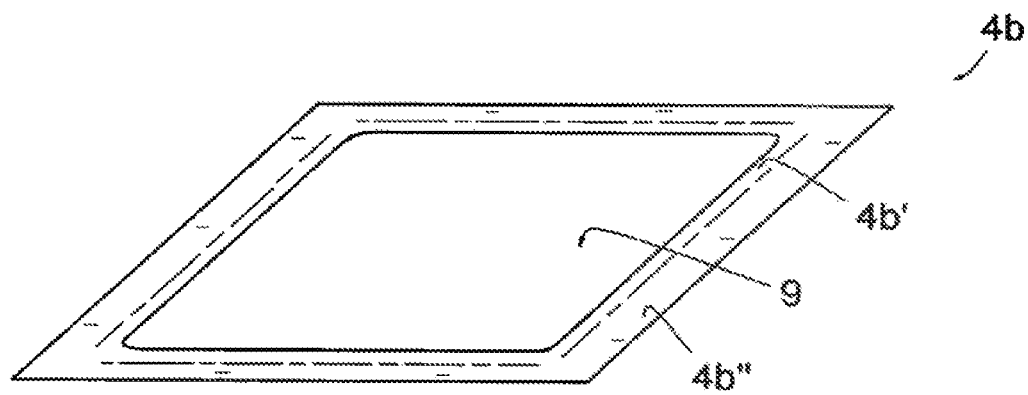
FIG. 2 is a perspective view of a lower sealing part of a sealing envelope also included in the packaging according to this first embodiment.

In reference to FIGS. 2 and 3A, the lower sealing part 4b is formed by a sheet of a material suited to protect the cover 3 against perforation.

For example, the lower sealing part 4b can be made of a flat or a thermoformed sheet of a material such as Tyvek®, HPDE, etc.

The desired stiffness of the upper and lower sealing parts can be adjusted by selecting an appropriate thickness for the sheet from which they are formed.

Said sealing part 4b comprises a frame 4b' delineating a central square or rectangular opening 9 and a bonding surface 4b" extending outwards, i.e. beyond the outer periphery of the frame 4b', for example, in a direction that could be substantially parallel to that the direction of the peripheral flange 7 and of the sealing cover 3. The central opening 9 allows the lower sealing part 4b to be inserted around the body 5 of the tub 2 until reaching the inferior surface of the flange 7, and the frame 4b' is adapted to be sealed to this inferior surface of the flange 7.

Figure 3B:
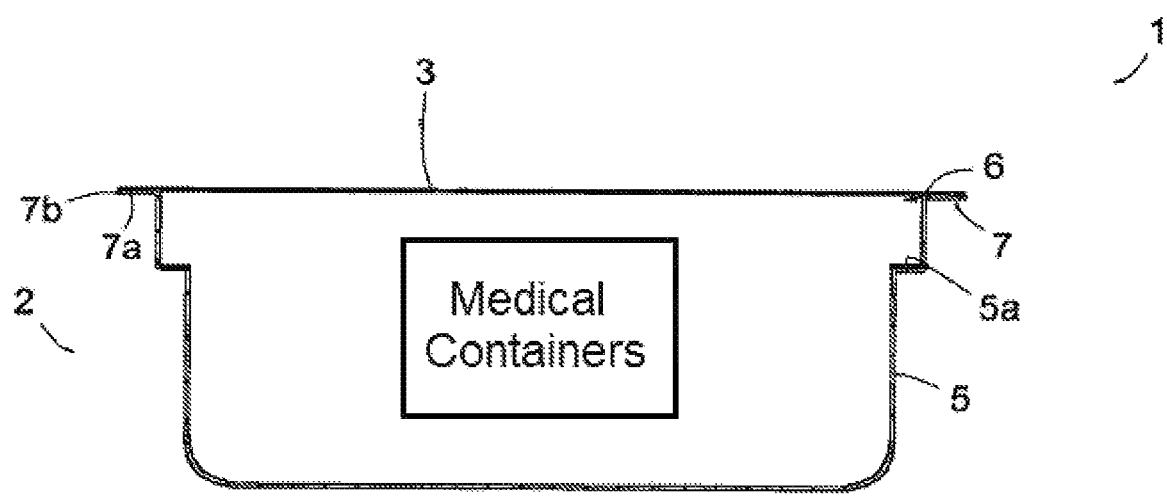
FIG. 3B is a side cross-section view of the tub of FIG. 3A taken along line 4-4.
Figure 4:
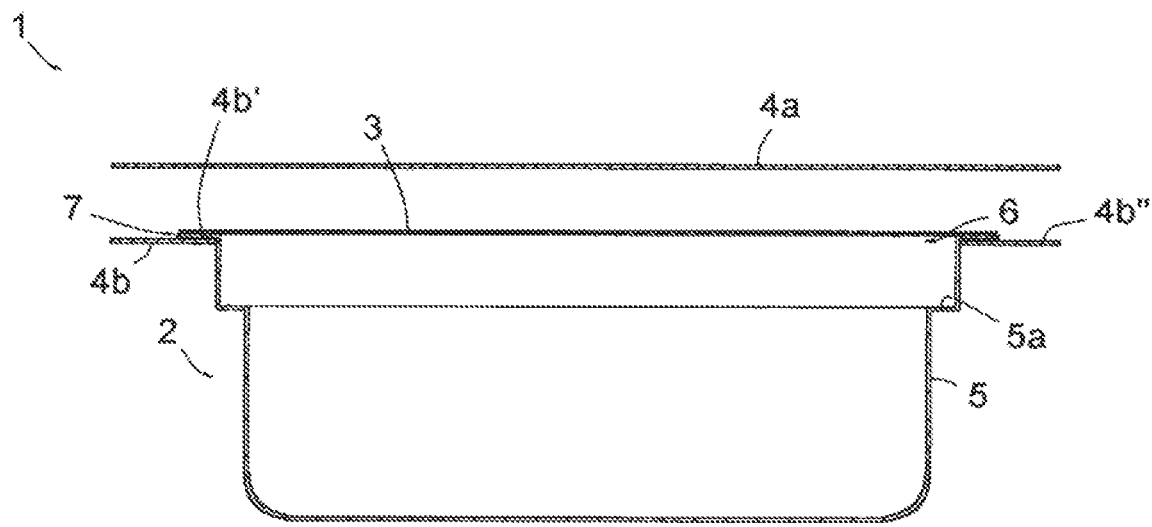
FIG. 4 is a view similar to FIG. 3A, said lower sealing part being bonded to the tub.
Figure 5:
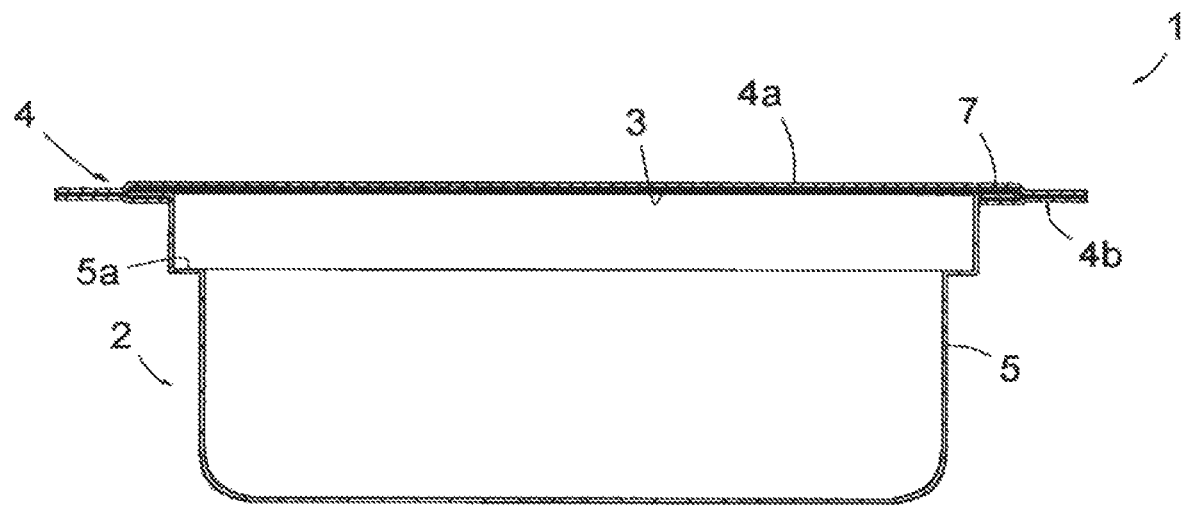
FIG. 5 is a view similar to FIG. 4, said upper sealing part being bonded to the tub and to the lower sealing part.

In use, the nest is placed in the tub 2 and the tub is sealed by the sealing cover 3 (shown in FIG. 3B). The lower sealing part 4b is then inserted around the body 5 and the frame 4b' thereof is bonded to the lower surface 7a (shown in FIG. 3A) of the flange 7 (FIG. 4); the separate upper sealing part 4a is then sealingly bonded to the bonding surface 4b" of the lower sealing part 4b (FIG. 5).

Thereafter, series of packagings 1 are stacked in boxes for transportation.

Figure 6:
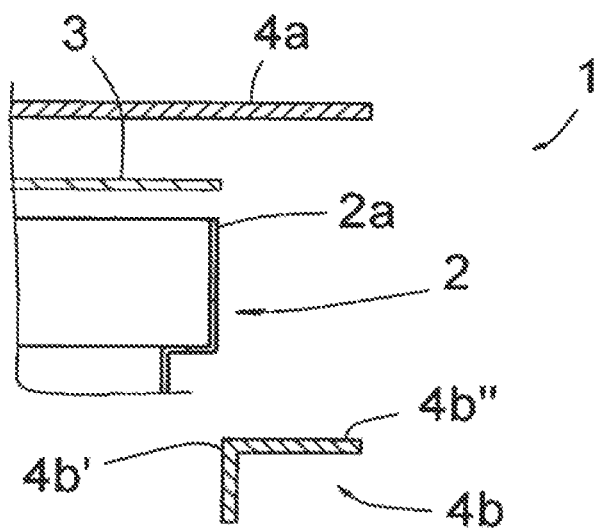
FIG. 6 is an enlarged, partial, side cross-section view of said upper and lower sealing parts according to a second embodiment, including a tub before the bonding of the upper and lower sealing parts to this tub.
Figure 7:
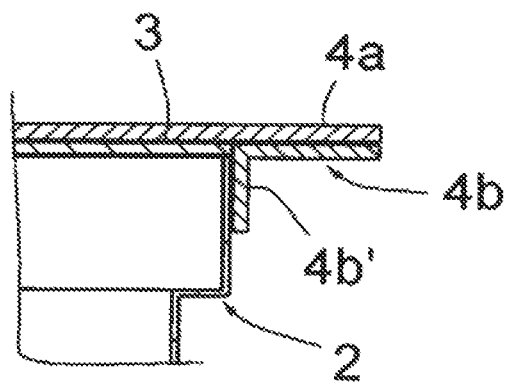
FIG. 7 is a view similar to FIG. 6 after the bonding of the upper and lower sealing parts to the tub.

According to the second embodiment shown on FIGS. 6 and 7, the upper peripheral wall 2a of the tub 2 has no peripheral outer flange, and the sealing cover 3 is bonded to the upper edge of this peripheral wall 2a.

The upper sealing part 4a is similar to the one of the embodiment shown on FIGS. 3A-5; it is formed of a sheet of a material suited to protect the sealing cover from perforation.

In this embodiment, the lower sealing part 4b exhibits a non-planar shape, wherein the frame 4b' is substantially parallel to the peripheral wall of the tub so as to surround the peripheral wall 2a of the tub 2 and to be sealed thereto (by bonding, stamping, gluing, welding). Further, the bonding surface 4b" is substantially perpendicular to the frame 4b' and substantially parallel to the sealing cover 3 and adapted to be sealed on the upper sealing part 4a.

Figure 8:
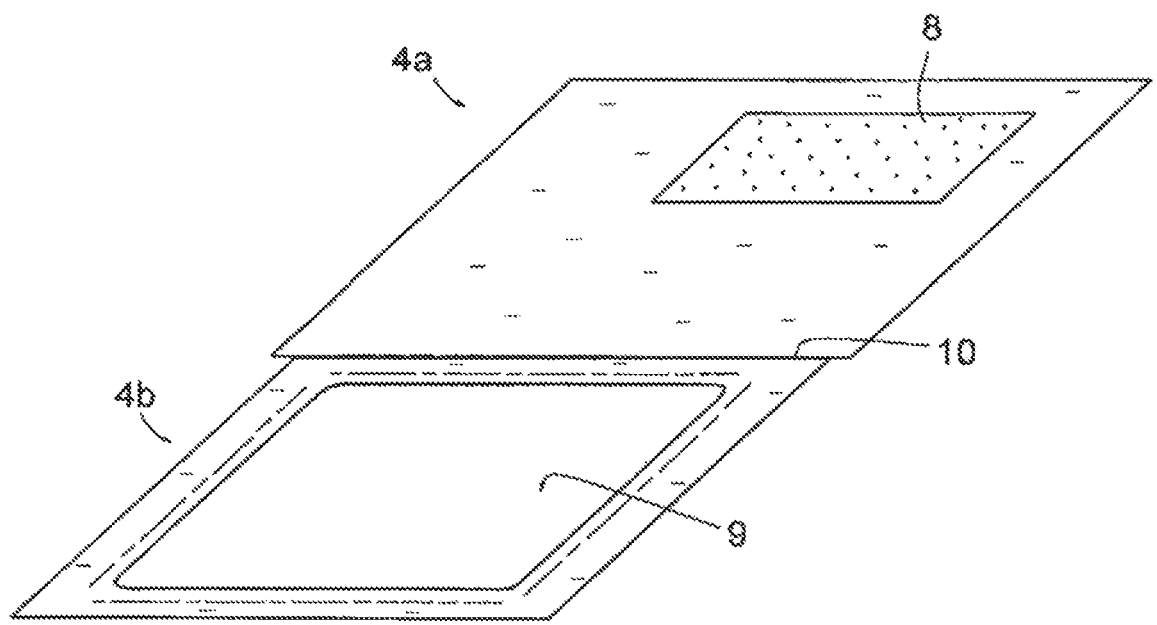
FIG. 8 is a perspective view of the sealing envelope similar to FIGS. 1 and 2, according to a third embodiment.

According to the third embodiment shown on FIG. 8, said upper sealing part 4a is connected to said lower sealing part 4b along a folding line or edge 10. The upper sealing part 4a is thus movable with respect to the lower sealing part 4b between an unfolded position, in which it does not prevent from sealing the lower sealing part 4b on the tub 2, and a folded position in which it is folded over said lower sealing part 4b and is able to be sealed to this lower sealing part 4b.

As it has become clear from the foregoing, the invention provides a packaging for containers, in particular for syringes or cartridges, having, with respect to the packaging of the prior art, the determining advantages of:

having no risk of perforation during transportation, thanks to the two upper and lower sealing parts 4a, 4b bonded one on the other;

being compact and saving space in the box, and providing rigid edges to the sealing envelope 4 thus avoiding an additional step of manually tensioning an opening edge at the time of opening the packaging.

The invention has been described above with reference to embodiments given by way of an example. Of course, it is not limited to these embodiments and extends to all other embodiments covered by the appended claims.

What is claimed is:

1. A packaging for medical containers, comprising:
    a tub configured to receive a plurality of medical containers therein, the tub having a peripheral wall and a flange extending from the peripheral wall;
    a sealing cover sealable on an opening of the tub, the sealing cover made from a permeable material that is permeable to a sterilization medium; and
    a sealing envelope for protecting the sealing cover against perforation, wherein the sealing envelope comprises:
        a lower sealing part, comprising:
            a frame defining an aperture therethrough and having an outer peripheral portion, the aperture adapted to receive at least a portion of the tub, the frame adapted to be sealed to a lower surface of the flange of the tub extending from the peripheral wall of the tub, and
            a bonding surface that extends outwards from the frame, the outer peripheral portion of the frame extending parallel to an outer periphery of the sealing cover, and
        an upper sealing part adapted to be sealed on the bonding surface and to cover the opening of the tub and the sealing cover, wherein the lower sealing part and the upper sealing part are at least partially separate from one another prior to sealing the upper sealing part to the bonding surface; and
    wherein the upper sealing part comprises a window made of the permeable material, wherein the window is permeable to the sterilization medium, and
    wherein the lower sealing part is a flat sheet.

2. The packaging of claim 1, wherein the lower sealing part includes an inner peripheral portion forming the frame, the outer peripheral portion of the frame forming the bonding surface, the bonding surface extending beyond an outer edge of the flange when the lower sealing part is sealed to the lower surface.

3. The packaging of claim 1, wherein the upper sealing part is another flat sheet.

4. The packaging of claim 3, wherein the lower and upper sealing parts are formed from a single piece of flat material and are connected to one another through a folding edge.

5. The packaging of claim 1, wherein the lower sealing part and the upper sealing part are a thermoformed material, and wherein the lower sealing part and the upper sealing part are configured to be bonded to one another via heat sealing.

6. The packaging of claim 1, wherein the lower sealing part and/or the upper sealing part are made of a heat sealable material, or are coated with a heat-sealable material, so that the lower sealing part is able to be heat sealed to the flange.

7. The packaging of claim 1, wherein the lower sealing part and the upper sealing part are mutually bonded with an adhesive.

8. The packaging of claim 1, wherein the permeable material of the sealing cover and the window comprises high-density polyethylene fibers.

* * * * *